United States Patent
Vickery, Jr. et al.

(10) Patent No.: US 10,408,771 B2
(45) Date of Patent: Sep. 10, 2019

(54) MERCURY-IN-PIPE ASSESSMENT TOOL AND METHOD OF USING THE SAME

(71) Applicant: Process Mercury Group LLC, Houston, TX (US)

(72) Inventors: James H. Vickery, Jr., Houston, TX (US); Patrick L. Laine, Pearland, TX (US); Daniel Dietrich, Livermore, CA (US); Lynn Essman, Cedar Park, TX (US); Gary M. Kane, Folsom, LA (US)

(73) Assignee: PROCESS MERCURY GROUP LLC, Houston, TX (US)

( * ) Notice: Subject to any disclaimer, the term of this patent is extended or adjusted under 35 U.S.C. 154(b) by 175 days.

(21) Appl. No.: 15/642,648

(22) Filed: Jul. 6, 2017

(65) Prior Publication Data
US 2018/0011034 A1    Jan. 11, 2018

Related U.S. Application Data

(60) Provisional application No. 62/359,269, filed on Jul. 7, 2016.

(51) Int. Cl.
| | | |
|---|---|---|
| *G01N 23/00* | (2006.01) | |
| *G01N 23/02* | (2006.01) | |
| *G01N 23/222* | (2006.01) | |
| *G21B 1/19* | (2006.01) | |
| *G21K 5/04* | (2006.01) | |

(52) U.S. Cl.
CPC .......... *G01N 23/025* (2013.01); *G01N 23/222* (2013.01); *G21B 1/19* (2013.01); *G21K 5/04* (2013.01); *G01N 2223/0745* (2013.01); *G01N 2223/1066* (2013.01); *G01N 2223/652* (2013.01)

(58) Field of Classification Search
CPC ..... G01N 2223/652; G01N 2223/1066; G01N 2223/0745; G01N 23/025; G01N 23/222; G21K 5/04; G21B 1/19
See application file for complete search history.

(56) References Cited

U.S. PATENT DOCUMENTS

| | | | | |
|---|---|---|---|---|
| 5,781,602 | A * | 7/1998 | Fero | B23K 31/12 376/159 |
| 2003/0152186 | A1 * | 8/2003 | Jurczyk | G21B 1/19 376/109 |
| 2010/0235018 | A1 * | 9/2010 | Christ | G01N 21/952 701/2 |
| 2012/0103069 | A1 * | 5/2012 | Al-Qahtani | G01M 3/243 73/40.5 A |
| 2016/0299236 | A1 * | 10/2016 | Ambrose-Thurman | G01T 1/175 |

* cited by examiner

*Primary Examiner* — Kiho Kim
(74) *Attorney, Agent, or Firm* — Carlson, Gaskey & Olds, P.C.

(57) ABSTRACT

A system according to an exemplary aspect of the present disclosure includes, among other things, a generator-detector configured to be attached to a pipe. The generator-detector is configured to measure the concentration of mercury in the pipe in a non-destructive manner. A method is also disclosed.

19 Claims, 2 Drawing Sheets

US 10,408,771 B2

MERCURY-IN-PIPE ASSESSMENT TOOL AND METHOD OF USING THE SAME

RELATED APPLICATIONS

This application claims the benefit of U.S. Provisional Application No. 62/359,269, filed Jul. 7, 2016, the entirety of which is herein incorporated by reference.

BACKGROUND

This disclosure relates to a Mercury-in-Pipe Assessment Tool (MiPAT) for non-destructive analysis of all forms of mercury (Hg) present in process equipment including but not limited to vessels, piping, hoses, pumps, exchangers, and all types of pipelines. The MiPAT of this disclosure provides oil and gas producers, for example, with the ability to cost-effectively assess and monitor the concentration and distribution of adsorbed, absorbed, chemisorbed, and free liquid phase mercury in oil and gas production, gathering, and processing systems and pipelines including subsea pipelines.

Current methods for the measurement of mercury in pipe are limited. One common method includes using a field portable handheld x-ray spectrometer to analyze an open end of a pipe or a coupon, which is a section of pipe that has been removed. Another technique involves pipe coupon digestion using a wet chemistry method, such as acid digestion, to prepare pipe coupons for analysis by AFS (atomic fluorescence spectroscopy) or AAS (atomic absorption spectroscopy), as examples. Another known method includes thermal desorption of a pipe coupon at about 800° C. to prepare the sample for analysis by AFS or AAS.

SUMMARY

A system according to an exemplary aspect of the present disclosure includes, among other things, a generator-detector configured to be attached to a pipe. The generator-detector is configured to measure the concentration of mercury in the pipe in a non-destructive manner.

In a further non-limiting embodiment of the foregoing system, the pipe is a portion of a pipeline for transporting oil or gas.

In a further non-limiting embodiment of any of the foregoing systems, the pipe is a portion of a subsea pipeline.

In a further non-limiting embodiment of any of the foregoing systems, the generator-detector includes a spectroscopic beam generator-detector.

In a further non-limiting embodiment of any of the foregoing systems, the generator-detector is configured to measure the concentration of mercury at two locations within the pipe, and the generator-detector is configured to average the two measurements.

In a further non-limiting embodiment of any of the foregoing systems, the two locations are about 180 degrees apart from one another.

In a further non-limiting embodiment of any of the foregoing systems, the generator-detector uses neutron activation analysis.

In a further non-limiting embodiment of any of the foregoing systems, the generator-detector includes a thermal neutron source and a gamma detector.

In a further non-limiting embodiment of any of the foregoing systems, the system further includes at least one magnet configured to mechanically couple the generator-detector to the pipe.

In a further non-limiting embodiment of any of the foregoing systems, the generator-detector is configured to measure mercury in the pipe down to a lower detection limit of 10 mg/kg±30%.

In a further non-limiting embodiment of any of the foregoing systems, the generator-detector is configured to measure mercury in the pipe to a lower detection limit down to at least 10 ppm±50%.

In a further non-limiting embodiment of any of the foregoing systems, the generator-detector is configured to measure mercury in the pipe to a lower detection limit down to 1 ppm±50%.

In a further non-limiting embodiment of any of the foregoing systems, the generator-detector is configured for use underwater at a depth down to at least 75 meters (about 250 feet).

A method according to an exemplary aspect of the present disclosure includes, among other things, mechanically coupling a device to a pipe, and measuring the concentration of mercury in the pipe using the device in a non-destructive manner.

In a further non-limiting embodiment of the foregoing method, the pipe is a subsea pipe, and wherein the device is initially positioned on the pipe by a diver.

In a further non-limiting embodiment of any of the foregoing methods, the device includes a generator-detector.

In a further non-limiting embodiment of any of the foregoing methods, the generator-detector includes at least one of a spectroscopic beam generator-detector, a thermal neutron source, and a gamma detector.

In a further non-limiting embodiment of any of the foregoing methods, the generator-detector is configured to measure mercury in the pipe to a lower detection limit down to at least 10 ppm±50%.

In a further non-limiting embodiment of any of the foregoing methods, the generator-detector is configured to measure mercury in the pipe to a lower detection limit down to 1 ppm±50%.

In a further non-limiting embodiment of any of the foregoing methods, the method includes deploying the device underwater at a depth down to at least 75 meters (about 250 feet).

DETAILED DESCRIPTION

The MiPAT of the present disclosure is a device (or combination of devices) that measures the concentration of mercury (Hg) within a pipe in a non-destructive manner. In particular, there is no need to harvest a pipe coupon when using the MiPAT. The MiPAT can be used to measure the concentration of mercury anywhere along the length of a piping run or pipeline.

Figure 1A:
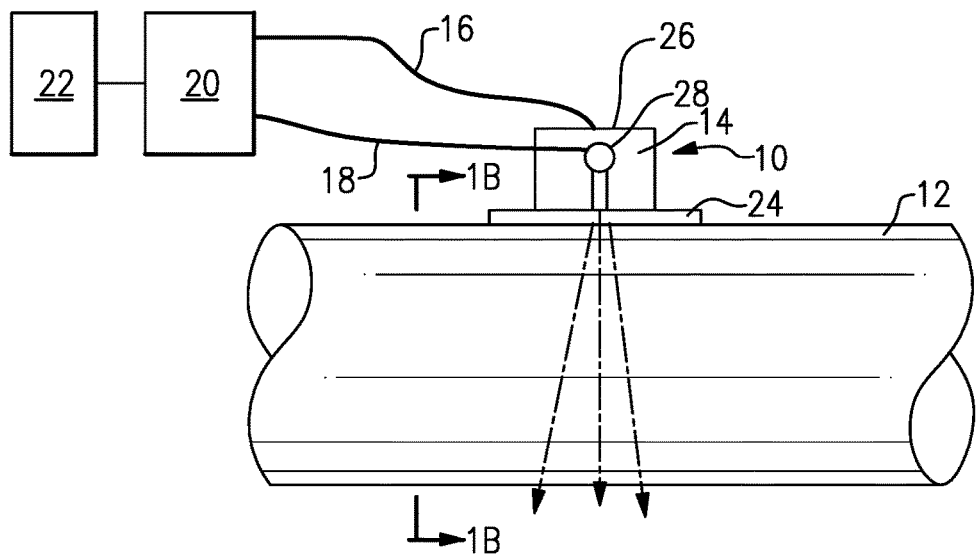
FIG. 1A is a side view of an example MiPAT arranged relative to a section of pipe.
Figure 1B:
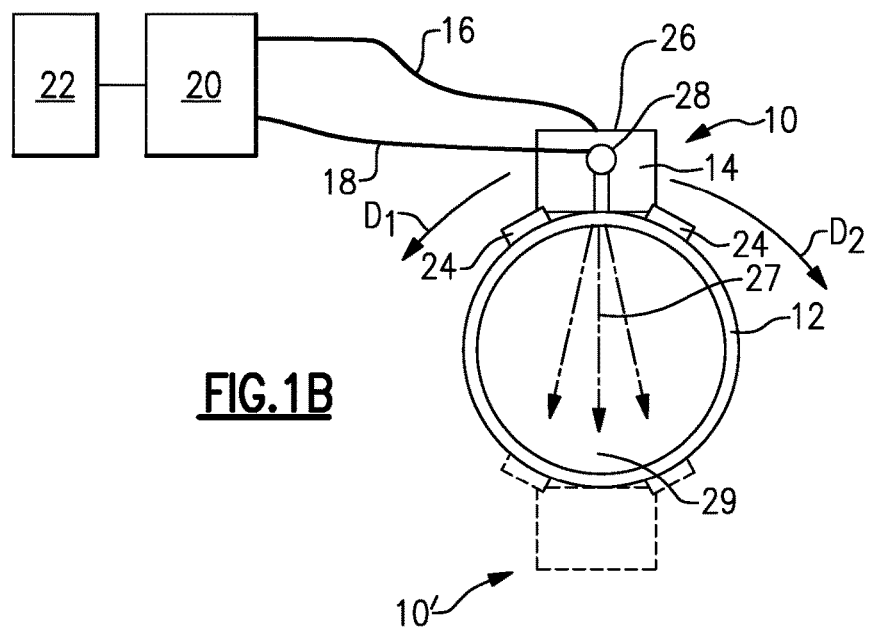
FIG. 1B is a sectional view taken along line 1B-1B in FIG. 1A and illustrates the detail of the arrangement between the MiPAT and the section of pipe.

FIG. 1A illustrates one example MiPAT 10 arranged relative to a pipe 12 viewed from a side. FIG. 1B is a cross-sectional view taken along line 1B-1B in FIG. 1A. As used in this disclosure, the term "MiPAT" is not a limiting term, and is used to refer to the device generally illustrated in FIGS. 1A-1B, which includes a number of interconnected devices and components.

In this example, the MiPAT 10 includes a generator-detector 14 electrically coupled to a data line 16 and a power line 18. The data line 16 and power line 18 can be provided in a single conduit, which can be a tether (sometimes referred to as an "umbilical cord"). It should be understood that the generator and the detector can be separate components. In this example, however, the separate generator and detector components are within the same unit. The generator-detector 14 generally speaking has a dual functionality and is configured to both generate a beam of energy, and in particular a beam of neutrons, configured to permeate the pipe 12 and to detect when that beam is reflected back to the generator-detector 14.

The data and power lines 16, 18 are in turn connected to a controller 20 or other computing unit and a power source 22 at a remote location. While in this example the MiPAT 10 is tethered to a remote location, such as a boat or rig, in some examples the MiPAT may be battery powered and communicate wirelessly with a remote computing unit to accomplish data transfer.

The controller 20 and power source 22 are illustrated schematically in the figures. It should be understood that the controller 20 could be part of a larger control module, or could alternatively be a stand-alone controller. Further, the controller 20 may be programmed with executable instructions for interfacing with and operating the various components of the MiPAT 10. The controller 20 additionally includes a processing unit and non-transitory memory for executing the various control strategies and modes of the MiPAT.

The generator-detector 14 in this example is mechanically coupled to an exterior of the pipe 12 by way of magnets 24. The magnets 24 are of a sufficient strength to couple the generator-detector 14 to the pipe 12, but do not interfere with the measurements of the generator-detector 14. While magnets 24 are shown, generator-detector 14 may be coupled to the pipe exterior using other techniques.

One example generator-detector 14 of this disclosure includes an exterior housing 26 attached to the magnets 24. A spectroscopic beam generator-detector 28 is provided within the housing 26. The magnets 24 are spaced-apart from one another, as shown in FIG. 1B, such that the spectroscopic beam generator-detector 28 can project energy in the form of a neutron beam, for example, from an exterior surface of the housing 26 toward the pipe 12 without interfering with the magnets 24.

In one example of use, once the MiPAT 10 is affixed to the pipe 12 in a location of interest, the controller 20 instructs the generator-detector 14 to take a measurement. In response to instructions from the controller 20, a neutron beam is generated and directed at the target location on the subject pipe. The neutron beam permeates the pipe 12. As noted above, the beam can permeate up to a 1-inch thick pipe wall. Mercury within the pipe 12 will cause a specific gamma energy response that is detected and measured by the detector. The generator-detector 14 is configured to generate a signal corresponding to the gamma energy spectra, and the controller 20 is configured to interpret this signal as a particular level of mercury within the pipe 12. Again, this is one example of use, and this disclosure extends to other examples.

In one example, the MiPAT 10 measures the concentration of total mercury at two points, 180 degrees apart, e.g. at pipe top 27 (e.g., the location closest to the MiPAT) and pipe bottom 29 (e.g., the location furthest from the MiPAT) of a particular section of pipe, and reports the concentration as an average of the two points. In another example, the MiPAT 10 is moveable, either manually or by an automated mechanism, circumferentially around the pipe in the directions D1, D2. The MiPAT is shown in phantom in FIG. 1B at a location near the pipe bottom, at 10'. The MiPAT may be moveable up to 360° around the pipe to obtain additional measurements. In some examples, only two measurements are taken from a single MiPAT position. In other examples, additional measurements are taken at additional MiPAT positions. Those measurements can be averaged, and the concentration may be reported as the average.

The MiPAT 10 has the capability of essentially "seeing through" a 1 inch thick pipe wall and measuring mercury down to a lower detection limit of 10 mg/kg±30%. Alternatively the MiPAT 10 can measure mercury down to a lower detection limit of 10 parts per million (ppm)±50%. In a further example, the MiPAT 10 can measure mercury down to a lower detection limit of 1 ppm±50%.

The MiPAT 10 in one example is configured for use underwater at depths down to 75 meters (about 250 feet). In other examples the MiPAT 10 is deployable to depths down to 100 meters (about 330 feet).

Another example generator-detector 14 uses neutron activation analysis. In that example, the generator-detector 14 includes a thermal neutron source (or generator) and a gamma detector that can operate with high resolution, high efficiency and without liquid nitrogen in confined spaces. Yet another example generator-detector 14 includes a radioactive source. Other example generator-detectors 14 includes a neutron generator and sodium iodide (NaI) detectors, and a high purity geranium (HPGe) detector. The generator-detectors 14 may be electromechanically cooled.

The generator-detector 14 may include a single detector and multiple sources, although this disclosure extends to generator-detectors having at least one source (generator) and at least one detector.

Figure 2:
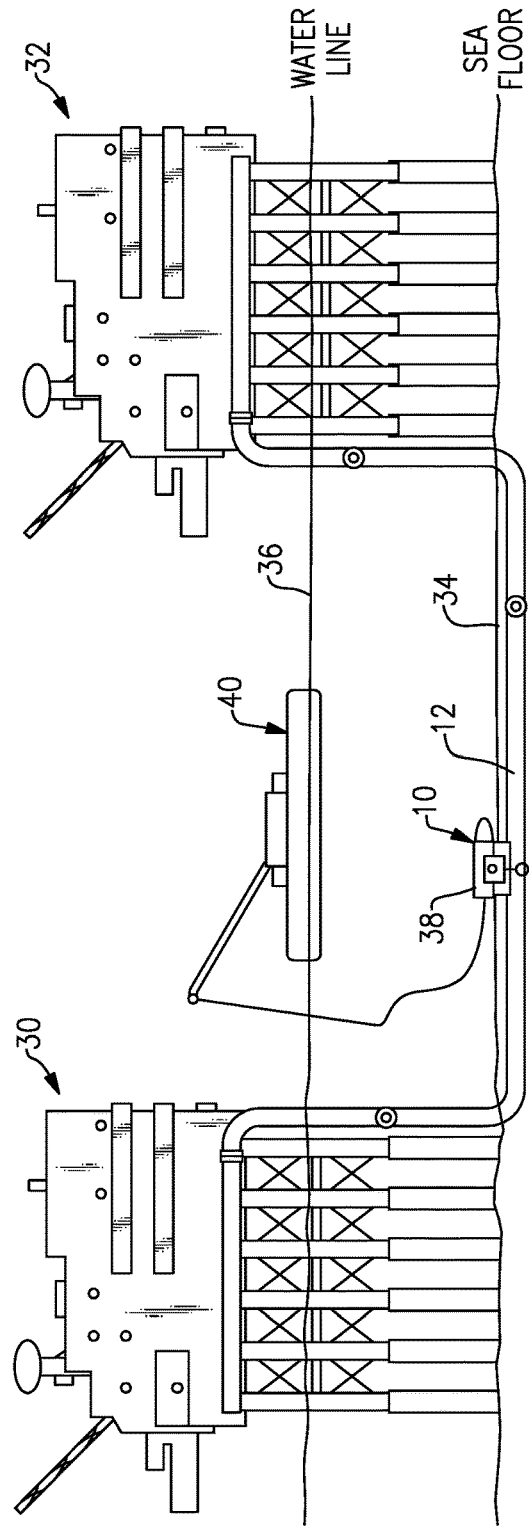
FIG. 2 illustrates the example MiPAT of FIGS. 1A-1B in use relative to a section of subsea pipeline.

With reference to FIG. 2, the MiPAT 10 is capable of being manually affixed to an exposed underground or underwater pipe 12, by way of the magnets 24, for example. In FIG. 2, the pipe 12 is fluidly coupled between two oil platforms 30, 32, and is sometimes referred to as a conductor pipe. The platforms 30, 32 project from the seafloor 34 above the water line (or water level) 36.

As shown in FIG. 2, a relatively long run of the pipe 12 is covered by mud at the seafloor 34 and may be encased in concrete. In those cases, the concrete and/or mud is removed by a dive team, for example, to expose the pipe 12 and allow for fixation of the MiPAT 10 relative to the pipe 12.

While the seafloor 34 and concrete adjacent the pipe 12 may need to be removed, a benefit of the MiPAT 10 is that the pipe 12 does not have to be cut, disassembled, or opened during the assessment process. In other words, the measurements of the present disclosure are taken in a non-destructive manner. In particular, since the present disclosure allows measurements to be taken in a non-destructive manner, measurements can be taken without requiring a system shutdown (e.g., the platforms 30, 32 can continue normal operations). These features reduce the risk of exposure to vapor inside the pipe 12, including mercury and/or hydrocarbon vapors, and reduces the time and effort required to obtain accurate and representative measurements of mercury in process piping and pipelines.

Referring back to FIG. 2, when used in subsea applications, the MiPAT includes a water proof housing 38 designed so that the generator-detector 14 can be deployed in water depths up to 100 meters for the assessment of subsea pipelines. The MiPAT can be deployed by divers or by a remotely operated vehicle (ROV) 40. When an ROV 40 is used, the ROV 40 can include the controller 20 and power source 22 in one example.

The MiPAT 10 of the present disclosure may be used to serve oil and gas operators in the decommissioning of mercury impacted offshore oil and gas production facilities and subsea pipelines. The MiPAT may also be used for the monitoring of mercury accumulation in operating pipelines. The MiPAT also provides oil and gas producers with an easily deployable tool for assessing the concentration and distribution of mercury along the length of any piping section or subsea pipeline ultimately providing a more accurate representative assessment of mercury in pipe. Specifically, while the MiPAT 10 is shown adjacent a section of the pipe 12 that is subsea, the MiPAT can be used to analyze the pipe 12 at locations above the seafloor 34 or above the water line 36.

To this end, while FIG. 2 shows the MiPAT 10 used in the context of offshore drilling, the MiPAT 10 is not limited to such uses, and can be used in other environments. For example, the MiPAT 10 can be used in scrap yard/smelter operations for rapid assessment and monitoring of steel pipe. The MiPAT 10 is also deployable on production platforms, processing plants, refineries, etc.

It should be understood that terms such as "generally," "substantially," and "about" are not intended to be boundaryless terms, and should be interpreted consistent with the way one skilled in the art would interpret those terms.

Although the different examples have the specific components shown in the illustrations, embodiments of this disclosure are not limited to those particular combinations. It is possible to use some of the components or features from one of the examples in combination with features or components from another one of the examples.

One of ordinary skill in this art would understand that the above-described embodiments are exemplary and non-limiting. That is, modifications of this disclosure would come within the scope of the claims. Accordingly, the following claims should be studied to determine their true scope and content.

The invention claimed is:

1. A system, comprising:
a generator-detector including an exterior housing configured to be attached to a pipe, the generator-detector including a spectroscopic beam generator-detector provided within the exterior housing and configured to measure the concentration of mercury in the pipe in a non-destructive manner.

2. The system as recited in claim 1, wherein the pipe is a portion of a pipeline for transporting oil or gas.

3. The system as recited in claim 2, wherein the pipe is a portion of a subsea pipeline.

4. The system as recited in claim 1, further comprising at least one magnet in direct contact with the exterior housing and the pipe such that the at least one magnet is configured to mechanically couple the exterior housing to the pipe.

5. The system as recited in claim 1, wherein the generator-detector is configured to measure mercury in the pipe down to a lower detection limit of 10 mg/kg±30%.

6. The system as recited in claim 1, wherein the generator-detector is configured to measure mercury in the pipe to a lower detection limit down to at least 10 ppm±50%.

7. The system as recited in claim 6, wherein the generator-detector is configured to measure mercury in the pipe to a lower detection limit down to 1 ppm±50%.

8. The system as recited in claim 1, wherein the generator-detector is configured for use underwater at a depth down to at least 75 meters (about 250 feet).

9. The system as recited in claim 1, wherein:
the exterior housing is connected to an underwater pipe adjacent a seafloor, and
the generator-detector is connected by a tether to a controller and a power source of a remotely operated vehicle adjacent a water line.

10. The system as recited in claim 1, wherein generator-detector is configured to measure the concentration of mercury in the pipe at a location where the mercury is circumferentially bound by a wall of the pipe.

11. A system, comprising:
a generator-detector configured to be attached to a pipe, the generator-detector configured to measure the concentration of mercury in the pipe in a non-destructive manner, and
wherein the generator-detector is configured to measure the concentration of mercury at two locations within the pipe, and wherein the generator-detector is configured to average the two measurements.

12. The system as recited in claim 11, wherein the two locations are about 180 degrees apart from one another.

13. The system as recited in claim 11, wherein the generator-detector uses neutron activation analysis.

14. The system as recited in claim 13, wherein the generator-detector includes a thermal neutron source and a gamma detector.

15. A method, comprising:
mechanically coupling a device to a pipe; and
measuring the concentration of mercury in the pipe using the device in a non-destructive manner to a lower detection limit of 1 ppm±50%.

16. The method as recited in claim 15, wherein the pipe is a subsea pipe, and wherein the device is initially positioned on the pipe by a diver.

17. The method as recited in claim 15, wherein the device includes a generator detector and the generator-detector includes at least one of a spectroscopic beam generator-detector, a thermal neutron source, and a gamma detector.

18. The method as recited in claim 15, wherein the step of mechanically coupling the device to the pipe includes using a magnet to mechanically couple the device to the pipe, the magnet directly contacting the pipe and an exterior housing of the device.

19. The method as recited in claim 15, wherein:
the step of measuring the concentration of mercury in the pipe includes measuring the concentration of mercury at two locations within the pipe and averaging the two measurements, and
the two locations are about 180 degrees apart from one another.

* * * * *